(12) United States Patent
Hill

(10) Patent No.: US 11,622,927 B2
(45) Date of Patent: Apr. 11, 2023

(54) CHANGING EYE COLOR BY GENE TRANSDUCTION

(71) Applicant: James W. Hill, Los Angeles, CA (US)

(72) Inventor: James W. Hill, Los Angeles, CA (US)

(73) Assignee: James W. Hill, Las Vegas, NV (US)

( * ) Notice: Subject to any disclaimer, the term of this patent is extended or adjusted under 35 U.S.C. 154(b) by 0 days.

(21) Appl. No.: 17/842,658

(22) Filed: Jun. 16, 2022

(65) Prior Publication Data
US 2022/0313585 A1 Oct. 6, 2022

Related U.S. Application Data

(62) Division of application No. 17/150,999, filed on Jan. 15, 2021, now Pat. No. 11,400,039.

(60) Provisional application No. 63/026,554, filed on May 18, 2020, provisional application No. 62/962,063, filed on Jan. 16, 2020.

(51) Int. Cl.
| | | |
|---|---|---|
| *C12N 15/864* | (2006.01) |
| *C12N 15/52* | (2006.01) |
| *A61K 48/00* | (2006.01) |
| *A61P 27/02* | (2006.01) |
| *A61K 8/60* | (2006.01) |
| *C12N 15/86* | (2006.01) |

(52) U.S. Cl.
CPC .............. *A61K 8/606* (2013.01); *C12N 15/86* (2013.01); *C12N 15/864* (2013.01)

(58) Field of Classification Search
None
See application file for complete search history.

(56) References Cited

U.S. PATENT DOCUMENTS

| | | | |
|---|---|---|---|
| 2004/0063652 A1* | 4/2004 | Jolly ...................... | C12N 15/86 514/44 R |
| 2005/0261234 A1* | 11/2005 | Dorey .................... | C07K 14/78 604/20 |
| 2010/0209477 A1 | 8/2010 | Butuner et al. | |
| 2011/0280909 A1 | 11/2011 | Moazed | |
| 2012/0265180 A1 | 10/2012 | Homer | |
| 2014/0288163 A1 | 9/2014 | Levy et al. | |
| 2018/0021170 A1 | 1/2018 | Haffner et al. | |
| 2019/0151409 A1 | 5/2019 | Blumenkranz et al. | |
| 2020/0179343 A1 | 6/2020 | Kandula | |

FOREIGN PATENT DOCUMENTS

| | | | |
|---|---|---|---|
| JP | H10-508491 | | 8/1998 |
| WO | WO 960232 | * | 7/1996 |
| WO | WO 2019/195423 A1 | | 10/2019 |

OTHER PUBLICATIONS

Aigner, B. et al., "Tyrosinase gene variants in different rabbit strains," Mammalian Genome, vol. 11, 2000, pp. 700-702.

Bertolotto, C. et al., "Regulation of Tyrosinase Gene Expression by cAMP in B16 Melanoma Cells Involves Two CATGTG Motifs Surrounding the TATA Box: Implication of the Microphthalmia Gene Product," The Journal of Cell Biology, vol. 134, No. 3, Aug. 1996, pp. 747-755.

Bordet, T. et al. "Ocular Gene Therapies in Clinical Practice: Viral Vectors and Nonviral Alternatives." Drug Discovery Today, vol. 24, No. 8, Aug. 2019, pp. 1685-1693.

Chinnery, H.R. et al., "Macrophage physiology in the eye," Pflugers Archiv—European Journal of Physiology, vol. 469 (3-4), Apr. 2017, pp. 501-515.

Daniels, G.A. et al., "A simple method to cure established tumors by inflammatory killing of normal cells," Nature Biotechnology, vol. 22, No. 9, Sep. 2004, pp. 1125-1132.

Ellis, B. L. et al., "A survey of ex vivo/in vitro transduction efficiency of mammalian primary cells and cell lines with Nine natural adeno-associated virus (AAV1-9) and one engineered adeno-associated virus serotype," Virology Journal, 10:74, Mar. 6, 2013, pp. 1-10.

Gallegos, J.E. et al., "Intron DNA Sequences Can Be More Important Than the Proximal Promoter in Determining the Site of Transcript Initiation," The Plant Cell, vol. 29, Apr. 2017, pp. 843-853.

Ganss, R. et al., "The Mouse Tyrosinase Gene," The Journal of Biological Chemistry, vol. 269, No. 47, Nov. 25, 1994, pp. 29808-29816.

Gargiulo, A. et al., "AAV-mediated Tyrosinase Gene Transfer Restores Melanogenesis and Retinal Function in a Model of Oculo-cutaneous Albinism Type I (OCA1)," Molecular Therapy, vol. 17, No. 8, Aug. 2009, pp. 1347-1354.

Hu, D. et al., "Role of Ocular Melanin in Ophthalmic Physiology and Pathology," Photochemistry and Photobiology, vol. 84, Mar. 2008, pp. 639-644.

Jungbluth, A.A. et al., "Expression of melanocyte-associated markers gp-100 and Melan-A/MART-1 in angiomyolipomas," Virchows Arch, vol. 434, May 1999, pp. 429-435.

Klüppel, M. et al., "The mouse tyrosinase promoter is sufficient for expression in melanocytes and in the pigmented epithelium of the retina," Proc. Natl. Acad. Sci. USA, vol. 88, May 1991, pp. 3777-3781.

Laties, A.M. et al., "Iris colour and relationship of tyrosinase activity to adrenergic innervation," Nature, vol. 255, May 8, 1975, pp. 152-153.

Laursen, A.B. et al., "Glucose, Pyruvate and Citrate Concentrations in the Aqueous Humour of Human Cataractous Eyes," Acta Ophthalmologica, vol. 52, Aug. 1974, pp. 477-489.

Le Poole, I.C. et al., "Presence of T Cells and Macrophages in Inflammatory Vitiligo Skin Parallels Melanocyte Disappearance," American Journal of Pathology, vol. 148, No. 4, Apr. 1996, pp. 1219-1228.

Mérida, S. et al., "Macrophages and Uveitis in Experimental Animal Models," Mediators of Inflammation, Jun. 2015, pp. 1-10.

(Continued)

*Primary Examiner* — Maria Marvich
(74) *Attorney, Agent, or Firm* — Fenwick & West LLP

(57) ABSTRACT

A person's iris color can lighten, such as from brown to lighter brown, green, hazel, or blue, by introducing a melanocyte-killing agent through the cornea of the person's eye and contacting the anterior surface of the iris with the agent at a dose sufficient to kill melanocytes in the iris stroma.

19 Claims, 5 Drawing Sheets
(4 of 5 Drawing Sheet(s) Filed in Color)

(56) References Cited

OTHER PUBLICATIONS

Quintero-Cadena, P. et al., "Enhancer sharing promotes neighborhoods of transcriptional regulation across eukaryotes," Genes|Genomes|Genetics Early Online, Oct. 31, 2016, pp. 1-10.
Sanchez-Perez, L. et al., "Killing of Normal Melanocytes, Combined with Heat Shock Protein 70 and CD40L Expression, Cures Large Established Melanomas," The Journal of Immunology, vol. 177, Sep. 15, 2006, pp. 4168-4177.
Sheppard, H.M. et al., "Recombinant Adeno-Associated Virus Serotype 6 Efficiently Transduces Primary Human Melanocytes Hilary," PLOS ONE, vol. 8, Iss. 4, e62753, Apr. 2013, pp. 1-7.
Shibata, K. et al., "Identification of a cis-Acting Element That Enhances the Pigment Cell-specific Expression of the Human Tyrosinase Gene," The Journal of Biological Chemistry, vol. 267, No. 29, Oct. 15, 1992, pp. 20584-20588.
Vile, R.G. et al., "In Vitro and in Vivo Targeting of Gene Expression to Melanoma Cells," Cancer Resarch, vol. 53, Mar. 1, 1993, pp. 962-967.
Vile, R.G. et al., "Use of Tissue-specific Expression of the Herpes Simplex Virus Thymidine Kinase Gene to Inhibit Growth of Established Murine Melanomas following Direct Intratumoral Injection of DNA," Cancer Research, vol. 53, Sep. 1, 1993, pp. 3860-3864.
Wakamatsu, K. et al., "Characterization of melanin in human iridal and choroidal melanocytes from eyes with various colored irides," Pigment Cell & Melanoma Research, vol. 21, Jun. 28, 2008, pp. 97-105.
Whelan, N. "Routes of Administration for Ocular Medications." Merck Manual Veterinary Manual, 2020, Content Last Modified Jan. 2015, 1 page.
Wilkerson, C.L et al., "Melanocytes and Iris Color," Arch Ophthalmology, vol. 114, Apr. 1996, pp. 1-6.
Reemann, P. et al., "Melanocytes in the Skin—Comparative Whole Transcriptome Analysis of Main Skin Cell Types," PLoS ONE 9(12), e115717, Dec. 29, 2014, pp. 1-17.

\* cited by examiner

CHANGING EYE COLOR BY GENE TRANSDUCTION

CROSS-REFERENCE TO RELATED APPLICATIONS

This application is a divisional of U.S. application Ser. No. 17/150,999, filed Jan. 15, 2021, which is now U.S. Pat. No. 11,400,039, which claims the benefit of U.S. Provisional Application Nos. 63/026,554, filed May 18, 2020, and 62/962,063, filed Jan. 16, 2020, each of which is incorporated herein by reference in its entirety.

FIELD

The subject technology relates generally to ophthalmology.

BACKGROUND

Some people want to change their eye color. Techniques such as colored contact lenses and colored discs implanted on the iris have been used to this end.

SUMMARY

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination and placed into a respective independent clause or into other of the independent clauses. Other clauses can be presented in a similar manner.

1.1 A method for changing a color of a subject's iris, comprising:
   introducing a melanocyte killing agent into the anterior chamber of an eye of the subject;
   thereby causing death to melanocytes and changing a color of the iris.
1. A method for changing a color of a subject's iris, comprising:
   introducing a gene vector into an anterior chamber of an eye of a subject;
   wherein the gene vector is capable of inducing death to melanocytes in a stroma of the iris of the eye, thereby changing a color of the iris.
2. The method of clause 1, wherein the introducing is performed from outside the anterior chamber, through an opening in the cornea of the eye, into the anterior chamber.
3. The method of clause 1, further comprising permitting the gene vector in the anterior chamber to contact the iris for a sufficient time to cause death to melanocytes in the stroma; and
   withdrawing an excess amount of the gene vector from the anterior chamber after the sufficient time has elapsed.
4. The method of clause 1, wherein the gene vector comprises a suicide gene.
5. The method of clause 4, wherein the suicide gene is thymidine kinase (tk) gene.
6. The method of clause 4, wherein the suicide gene is herpes simplex virus thymidine kinase (HSVtk) gene.
7. The method of any of clauses 4-6, wherein the gene vector further comprises a promoter regulating expression of the suicide gene.
8. The method of clause 7, wherein the promoter is a melanocyte-specific gene promoter, optionally wherein the melanocyte-specific gene promoter is tyrosinase (Tyr) promoter.
9. The method of clause 4, wherein the gene vector comprises a herpes simplex virus thymidine kinase (HSVtk) gene and a tyrosinase (Tyr) promoter.
10. The method of any of clauses 7-9, wherein the suicide gene and the melanocyte-specific gene promoter are carried on a plasmid.
11. The method of any of clauses 7-9, wherein the suicide gene and the melanocyte-specific gene promoter are carried by a viral vector, wherein the viral vector is selected from the group consisting of an adenovirus, an adeno-associated virus, and a lentivirus.
12. The method of any of clauses 7-9, wherein the suicide gene and the melanocyte-specific gene promoter are carried by an adeno-associated viral vector.
13. The method of clause 12, wherein the adeno-associated viral vector comprises a rAAV1 capsid or a rAAV6 capsid.
14. The method of clause 4, further comprising administering a nucleoside analog to the subject.
15. The method of clause 14, wherein the nucleoside analog is selected from the group consisting of ganciclovir, acyclovir, and valganciclovir.
16. A method for changing a color of a subject's iris, comprising contacting an anterior surface of the iris with a substance that kills melanocytes, thereby changing a color of the iris.
17. The method of clause 16, wherein the substance comprises an adeno-associated virus (AAV) carrying a herpes simplex virus thymidine kinase (HSVtk) gene under the control of tyrosinase (Tyr) promoter.
18. A composition for changing a color of a subject's iris, comprising:
   a sterile ophthalmic preparation comprising a genetic vector comprising a suicide gene under the control of a melanocyte-specific gene promoter that induces expression of the suicide gene in melanocytes.
19. The composition of clause 18, wherein the genetic vector comprises an adeno-associated virus.
20. The composition of clause 18 or 19, wherein the preparation is in a powder form, and is reconstitutable with a fluid to form a sterile ophthalmic solution or suspension.
21. A device for delivery of a biologic agent comprising (i) a biocompatible object configured to contact with a person's iris, and (ii) the composition of any one of clauses 18-20.
22. The device of clause 21, wherein the biocompatible object comprises a disc, strip, or pledget.
23. The composition of any of clauses 18-20, wherein the suicide gene is herpes simplex virus thymidine kinase (HSVtk) gene under the control of tyrosinase (Tyr) promoter.
24. A device for delivery of a biologic agent to an anterior surface of an iris, comprising:
   a flexible disc insertable through an incision in a cornea of a subject's eye and positionable at an anterior surface of the iris of the eye;
   wherein the disc has a pupillary opening therethrough, the opening positionable at the pupil of the eye when the disc is positioned at the anterior surface of the iris, thereby permitting aqueous humor to flow from the pupil of the eye through the pupillary opening;
a delivery material located at a posterior aspect of the disc, the material configured to contact the anterior surface of the iris and to release a genetic vector into a stroma of the iris; and
the genetic vector.
25. The device of clause 24, wherein the delivery material comprises a hydrogel.
26. The device of clause 24 or 25, wherein the genetic vector comprises an adeno-associated virus (AAV).
27. The device of any of clause 24-26, wherein the genetic vector comprises (a) a suicide gene and (b) a melanocyte-specific gene promoter that regulates expression of the suicide gene.
28. The device of clause 27, wherein the suicide gene is herpes simplex virus thymidine kinase (HSVtk) gene and the melanocyte-specific gene promoter is tyrosinase (Tyr) promoter.
29. The device of any of clause 24-28, further comprising:
a central protrusion extending in a direction posteriorly from the posterior aspect of the disc and being disposed adjacent to the pupillary opening;
wherein the central protrusion is configured to contact a peripupillary region of the iris when the disc is positioned at the anterior surface of the iris and while the subject's aqueous humor flows from the pupil of the eye through the pupillary opening.
30. The device of clause 29, wherein the central protrusion extends circumferentially around the pupillary opening.
31. The device of any of clause 24-28, further comprising:
a peripheral protrusion extending in a direction posteriorly from the posterior aspect of the disc and being disposed adjacent to a periphery of the disc;
wherein the peripheral protrusion is configured to contact a periphery of the iris when the disc is positioned at the anterior surface of the iris and while the subject's aqueous humor flows from the pupil of the eye through the pupillary opening.
32. The device of clause 31, wherein the peripheral protrusion extends circumferentially around the periphery of the disc.
33. The device of clause 29, further comprising:
a peripheral protrusion extending in a direction posteriorly from the posterior aspect of the disc and being disposed adjacent to a periphery of the disc;
wherein the peripheral protrusion is configured to contact a periphery of the iris when the disc is positioned at the anterior surface of the iris and while the subject's aqueous humor flows from the pupil of the eye through the pupillary opening.
34. The device of clause 31, wherein the peripheral protrusion extends circumferentially around the periphery of the disc.
35. The device of any of clause 24-34, wherein the disc is foldable, permitting insertion into an anterior chamber of the subject's eye through a corneal incision that is less wide than a largest diameter of the disc.
36. The device of any of clause 24-35, further comprising a tool configured to carry the disc into an anterior chamber of the subject's eye as a surgeon inserts the disc through a corneal incision.
37. An adeno-associated virus (AAV) having an AAV1 or AAV6 capsid and a construct comprising a suicide gene under the control of a promoter that induces expression of the suicide gene in melanocytes.
38. The AAV of clause 37, wherein the suicide gene is thymidine kinase (tk) gene.
39. The AAV of clause 37, wherein the suicide gene is herpes simplex virus thymidine kinase (HSVtk) suicide gene.
40. The AAV of any one of the clauses 37-39, wherein the promoter is tyrosinase (Tyr) promoter.
41. A pharmaceutical composition comprising the AAV of any one of the clauses 37-40 in an excipient.
42. A kit for changing an eye color, comprising the AAV of any one of the clauses 37-40 or the pharmaceutical composition of clause 41 and a nucleoside analog.
43. The kit of the clause 42, wherein the nucleoside analog is selected from the group consisting of ganciclovir, acyclovir, and valganciclovir.
44. The kit of any one of clauses 41-43, further comprising a device for delivery of the AAV or the pharmaceutical composition into melanocytes of a human subject.

In one aspect, the present disclosure provides a composition for changing a color of a subject's iris, comprising: a sterile ophthalmic preparation comprising a genetic vector carrying (a) a suicide gene; and (b) a melanocyte-specific gene promoter operably linked to the suicide gene.

In some embodiments, the genetic vector is selected from the group consisting of a plasmid, an adenovirus, an adeno-associated virus, and a lentivirus. In some embodiments, the genetic vector comprises a recombinant adeno-associated virus.

In some embodiments, the preparation is in a powder form, and is reconstitutable with a fluid to form a sterile ophthalmic solution or suspension. In some embodiments, the composition further comprises a biocompatible object configured to contact the preparation and sized to be placed in contact with a person's iris. In some embodiments, the biocompatible object comprises a disc, strip, or pledget.

In some embodiments, the suicide gene is selected from the group consisting of (i) a herpes simplex virus thymidine kinase gene; (ii) a cytosine deaminase gene; (iii) a nitroreductase gene; and (iv) a carboxypeptidase G2 gene. In some embodiments, the melanocyte-specific gene promoter comprises a tyrosinase (Tyr) promoter. In some embodiments, the suicide gene comprises a herpes simplex virus thymidine kinase (HSVtk) gene, and the melanocyte-specific gene promoter comprises a tyrosinase (Tyr) promoter.

In another aspect, the present disclosure provides a method for changing a color of a subject's iris, comprising: introducing a melanocyte-killing agent into the anterior chamber of an eye of a subject; wherein the agent causes apoptotic death to melanocytes in a stroma of the iris of the eye, thereby changing a color of the iris.

In yet another aspect, the present disclosure provides a method for changing a color of a subject's iris, comprising: introducing a gene vector into the anterior chamber of an eye of a subject; wherein the introducing of the gene vector results in death to melanocytes in a stroma of the iris of the eye, thereby changing a color of the iris.

In some embodiments, the step of introducing is performed from outside the anterior chamber, through an opening in the cornea of the eye, into the anterior chamber.

In some embodiments, the gene vector comprises a suicide gene. In some embodiments, the suicide gene is selected from the group consisting of (i) a herpes simplex virus thymidine kinase gene; (ii) a cytosine deaminase gene; (iii) a nitroreductase gene; and (iv) a carboxypeptidase G2 gene. In some embodiments, the gene vector comprises a viral thymidine kinase (tk) suicide gene. In some embodiments, the gene vector comprises a herpes simplex virus thymidine kinase (HSVtk) gene. In some embodiments, the suicide gene is operably linked to a melanocyte-specific gene promoter. In some embodiments, the suicide gene is operably linked to a melanocyte-specific gene promoter for tyrosinase (Tyr). In some embodiments, the suicide gene comprises a herpes simplex virus thymidine kinase (HSVtk) gene operably linked to a melanocyte-specific gene promoter for tyrosinase (Tyr).

In some embodiments, gene vector is selected from the group consisting of a plasmid, an adenovirus, an adeno-associated virus, and a lentivirus. In some embodiments, the gene vector comprises a recombinant adeno-associated virus. In some embodiments, the recombinant adeno-associated virus comprises an AAV1 or an AAV6 capsid protein.

In some embodiments, the method further comprises administering a nucleoside analog to the subject. In some embodiments, the method further comprises maintaining miosis of the pupil of the eye of the subject during the introducing. In some embodiments, the nucleoside analog is ganciclovir, acyclovir, or valganciclovir.

In one aspect, the present disclosure provides a method for changing a color of a subject's iris, comprising contacting an anterior surface of the iris with a substance that kills melanocytes, thereby changing a color of the iris. In some embodiments, the substance comprises a recombinant adeno-associated virus (rAAV) comprising a herpes simplex virus thymidine kinase (HSVtk) gene that is operably linked to a gene promoter for tyrosinase (Tyr).

In one aspect, the present disclosure provides use of a gene vector for changing a color of a subject's iris, wherein the gene vector comprises (a) a suicide gene; and (b) a melanocyte-specific gene promoter operably linked to the suicide gene.

In another aspect, the present disclosure provides a gene vector for use in changing a color of a subject's iris, wherein the gene vector comprises (a) a suicide gene; and (b) a melanocyte-specific gene promoter operably linked to the suicide gene.

In yet another aspect, the preset disclosure provides a composition for changing a color of a subject's iris, comprising a sterile ophthalmic preparation comprising a genetic vector carrying a nucleic acid that is capable of inducing death of melanocytes in the iris when administered into an eye.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is a side perspective view of gene vector delivery disc.

FIG. 1B is a sectional view of gene vector delivery disc, with a pupillary and limbal guard.

FIG. 1C is a sectional view of gene vector delivery disc, with a pupillary guard.

FIG. 1D is a sectional view of gene vector delivery disc positioned in contact with an iris of an eye.

DETAILED DESCRIPTION

Figure 1A:
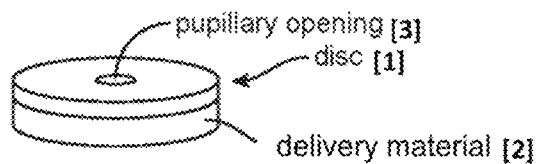
FIGS. 1A through 1D show various embodiments of a gene vector delivery disc.

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa. To the extent permitted by law, the contents of this disclosure, including any figures and text, are protected under U.S. copyright law, copyright 2019.

Changing Eye Color

Iris color plays a significant social function as an attribute of beauty. Alteration of some types of iris color has become possible using colored contact lenses. These lenses can have a prescriptive optical power or can serve a cosmetic function only.

There are several disadvantages associated with use of colored contact lenses for cosmetic purposes. The lenses have the same potential complications of use as contact lenses with prescriptive optical powers, including allergic reactions to the lens material and infections from improper handling. Further, contact lenses cannot be tolerated by some potential users due to discomfort. Additionally, colored contact lenses require a degree of dexterity to insert and remove that is not possessed by all potential users. Further, permanent changes in iris color cannot be achieved through the use of colored contact lenses. Moreover, colored contact lenses often fail to provide a natural-looking, cosmetically acceptable effect. Whereas natural brown irises are opaque, natural blue, gray, violet, and green irises are not. When a blue or green contact lens is placed over a brown iris, however, an opaque blue or and green iris is presented. Because this condition does not exist in nature, the iris appears fake and is not cosmetically appealing.

Other methods for altering iris color involves the use of colored discs implanted anteriorly to the iris, or pigments injected into the iris. Because of the potential complications of these invasive ocular procedures and of leaving a foreign body within the eye, and because of an unnaturally opaque appearance of the iris after these interventions, the implantation of colored iris implants and insertion of pigments into the iris have not been widely adopted.

Yet another method to alter iris color is applying laser energy to the eye, which removes some pigmented tissue from the front of the iris. Potential problems with this method include scarring of the iris from excessive heat transfer, disruption of iridial proteins and of fine structures of the iris (e.g., stromal crypts and furrows) that contribute to eye color, and postoperative glaucoma from dislodged iris fragments that clog the eye's trabecular meshwork, responsible for draining aqueous humor from the anterior chamber to maintain normal intraocular pressure. Moreover, laser light is potentially difficult to safely administer near the pupil, due to a risk of transmitting laser energy to the back of the eye and damaging the retina or optic nerve.

Thus, there remains a need for a method to alter human iris color safely and permanently that does not require colored contact lenses, implanted lenses, pigment deposition in the iris, or lasering of the iris.

Iris and Color

The iris consists of five cell layers, the anterior border layer, stroma, the sphincter and dilator muscles fibers, and the posterior pigment epithelium, of which the most important for the appearance of eye color are the anterior layer and its underlying stroma. Embryological studies of eye formation demonstrate that the two pigmented layers of the iris are derived from different sources. The posterior layer is known as the iris pigment epithelium (IPE) and consists of a double layer of cuboidal pigmented cells that are tightly fused. These are of neuroectodermal origin, coming from the anterior extremity of the optic cup. In contrast to the IPE, the stromal melanocytes are of the same embryological origin as the dermal melanocytes, in the neural crest, and migrate through the uveal tract during development. The IPE is always pigmented in the examination of the iris in all eye colors, except in people with albinism, and contributes little to the impression of eye color. Where the above-lying stroma is thin, this layer can have some influence on patterning. For example, the dark coloration of the IPE can absorb the penetrating light in eyes with a very thin stroma, which will give the white collagen fibers in the deeper cell layers of the stroma a grey tinge.

The IPE may serve a protective role for the retina by absorbing excess light that can only enter through the pupil and is not able to be reflected back out. Non-pigmented smooth muscle differentiated tissue at the stromal-IPE junction acts as the iris dilator muscle. The two top cell layers in the iris represent the major component of the iris. The exterior anterior border layer is extremely thin, especially when it is not pigmented and consists of modified stroma cells, i.e., a dense collection of fibroblasts, melanocytes, and radially oriented collagen fibers.

The underlying stroma consist of loose connective tissue that is made up of fibroblasts, melanocytes, collagen fibril protein (type I, III; VI and XVIII), glycosaminoglycans, and immunological cells, such as macrophages and mast cells. The dendrites of the stromal melanocytes are generally oriented parallel to the iris surface, tending to cluster in the anterior boarder layer and have been shown to represent approximately 66% of the iris stromal cells, irrespective of eye color.

The common occurrence of lighter iris colors is found almost exclusively in Europeans and individuals of European admixture, although it has been reported sporadically in other populations. The number of melanocytes does not appear to differ between different eye colors, however it has been reported that the total number of melanocytes may be less in Asian irides compared with those of African or Europeans ancestry, due to a smaller iris area or slightly lower melanocyte density. Ultrastructural studies of the iridial stromal melanocytes have revealed that differences in perceived eye color are the result of variable amounts and qualities of the melanosome particles in which the melanin pigment is packaged within these cells.

There are two types of melanin pigments that contribute to eye color: eumelanin, which has a blackish brown color, and pheomelanin/lipochrome, which has a reddish yellow color. Everyone has eumelanin in the back of their iris, except those with albinism, who have little or no pigment in their skin or eyes. The type and amount of melanin in the front of the iris are important to eye color by reflecting light of various colors.

Unlike skin and hair, in which melanin is continuously produced and secreted, in the iris, melanosomes are retained and congest the cytoplasm of the melanocytes within the iris stroma. The quality of the melanin between eye colors has also been studied chemically, blue irides have been reported to have minimal pigment content whereas eumelanic and pheomelanic forms have been detected in other eye colors. Notably, the quantity and type of melanin have also been correlated with iris color, with the eumelanin:pheomelanin ratio much greater for darker eyes, whereas lighter eyes demonstrated slightly greater amounts of pheomelanin. Thus, melanin pigment quantity, packaging, and quality all vary, giving a spectrum of eye shades.

Studies have shown that the number of melanocytes, the proportion of melanocytes among all cells (including fibroblasts) in the iris stroma, and iris stromal cellularity are not major contributors to iris color.

Rather, differences in iris colors are at least partially attributable to variable average melanosomal area per perinuclear cytoplasmic area (AMAC) and average number of melanosomes per perinuclear area (AMNC) within superficial iris melanocytes. This result reflects the large difference between uniformly blue eyes and all other color groups. Specifically, among autopsy eyes classified as uniform-blue, uniform-hazel, uniform-brown, or any showing a darker peripupillary ring, electron microscopic images and computerized image analysis, area, number, and size of mature melanosomes within the perinuclear cytoplasmic area only or within perinuclear and peripheral cytoplasmic areas of the superficial stromal melanocytes combined were measured, leading to the above-cited findings.

Eye Color Genetics

The presence of melanin within the iris is responsible for human eye coloration with complex patterns also evident in this tissue, including Fuchs' crypts, nevi, Wolfflin nodules and contraction furrows. Although segregation of blue-brown eye color has been described using a simple Mendelian dominant-recessive gene model, a modern molecular genetic perspective takes into consideration biological complexities of this process as a polygenic trait. Approximately 74% of the variance in human eye color is thought to be explained by one interval on chromosome 15 that contains the OCA2 gene. Fine mapping of this region has identified a single base change, rs12913832 T/C within intron 86 of the upstream HERC2 locus that explains almost all of this association with blue-brown eye color. This SNP, serving as a target site for the SWINF family member HLTF, acts as part of a highly evolutionary conserved regulatory element required for OCA2 gene activation through chromatin remodeling. Major candidate genes possibly affecting iris patterns also include MITF and PAX6.

Suicide Gene Transduction to Kill Melanocytes

As used herein, a "suicide gene" is a polynucleotide encoding a protein that causes a cell to kill itself, typically through apoptosis, i.e., programmed cell death, or by any other cytotoxic mechanism. Activation of these genes can be due to many processes, but the main cellular "switch" to induce apoptosis is the p53 protein. Suicide genes are also called prodrug transforming genes, as they encode proteins that can transform the nontoxic prodrug substrates into toxic drugs. For example, the nontoxic 5F-cytosine (5Fc) can be transformed into cancer toxic 5F-uracil (5Fu) by the cytosine deaminase (CD) from *Escherichia coli*.

Suicide gene therapy using deactivated drugs to kill cells are known as gene-directed enzyme prodrug therapy (GDEPT) or gene-prodrug activation therapy (GPAT).

GDEPT utilizes a gene encoding a foreign enzyme delivered to the tumor, after which a prodrug is administered and activates a cytotoxic drug that has been expressed in the tumor. Three of the most promising suicide gene/prodrug (e.g., nucleoside analogs) combinations are (1) herpes simplex virus thymidine kinase (HSV1-TK) with ganciclovir (GCV), (2) cytosine deaminase (CD) with 5-fluorocytodine (5-FC), and (3) bacterial nitroreductase (NTR) with 5-(azaridin-1-yl)-2,4-dinitrobenzamide (CB 1954).

Another example of GDEPT is the CPG2-CMDA system, a suicide gene therapy based on the bacterial enzyme carboxypeptidase G2 (CPG2). CPG2 has the advantage over the well-studied suicide genes HSV-TK and CD in that it activates prodrugs that are able to kill quiescent as well as proliferating cells. CPG2 cleaves the prodrug CMDA such that its cytotoxic drug is directly released and has the advantage that no further enzymatic processing is required for drug activation.

Intradermal injections of a plasmid in which the HSV thymidine kinase (HSVtk) suicide gene is transcriptionally targeted to melanocytes through the tyrosinase promoter (Tyr-HSVtk) leads to tissue specific killing of melanocytes on administration of the nucleoside analog prodrug ganciclovir (GCV), with minimal inflammation. A combination of multiple dermal injections of the Tyr-HSVtk plasmid with a plasmid expressing the murine heat shock protein 70 (hsp70) gene (CMV-hsp70) generates localized killing of normal melanocytes within a highly inflammatory environment. Fortunately, simple killing of melanocytes is very poorly effective at generating anti-melanocyte/melanoma T cell responses in vivo, reducing the risk of an autoimmune response, such as vitiligo.

DNA injection facilitates targeted expression to pigment-producing melanocytes within the bulb matrix of the hair follicles. Transcription of the tyrosinase gene occurs specifically in melanogenic cells in the hair bulb during the anagen stage of the hair cycle, when cells proliferate and hair fiber production occurs. The promoter of the tyrosinase gene can direct melanocyte- and melanoma-specific gene expression of therapeutic transgenes, e.g., for the treatment of melanoma. The hair follicle constitutes an area of immune privilege (i.e., immune responses are limited or prevented). Loss of this immune privilege may be involved in pathologies, such as alopecia areata, which is characterized by patchy hair loss and is believed to be caused by an autoimmune response to hair follicles in the anagen phase.

Immunogenic killing of tumor cells is associated with induction of hsp, which can serve as an effective switch to convert tolerogenic presentation of self-antigens by dendritic cells (DCs) into highly immunostimulatory presentation sufficient to break immunological tolerance. Intradermal plasmid DNA injections to deliver a transcriptionally targeted cytotoxic gene, along with heat shock protein (hsp), can be used in mice to induce direct in vivo inflammatory killing of normal melanocytes. When combined with hsp administration via a plasmid, highly specific killing of normal cells can be used to break immunological tolerance to self-antigens and leads to the rejection of established systemically distributed tumors. However, the anti-self T-cell response is also rapidly suppressed in vivo, presumably as a safeguard against the development of autoimmune disease in circumstances wherein pathological killing of normal cells occurs.

Intradermal injection of Tyr-HSVtk DNA targets melanocytes. To target cytotoxic gene expression to melanocytes, a plasmid or other vector carrying the herpes simplex virus thymidine kinase (HSVtk) gene transcriptionally controlled by the tyrosinase promoter (Tyr-HSVtk) can be constructed. Injection of a tyrosinase promoter-lacZ plasmid leads to expression specifically at the base of hair shafts where melanocytes are located. Expression of tyrosinase is specific to melanocytes, and loss of its expression can be used as a surrogate marker of melanocyte destruction. Upon provision of the prodrug ganciclovir (GCV) (or other suitable nucleoside analog), a cell expressing HSVtk converts GCV to its toxic triphosphate form, which, when incorporated into DNA during synthesis, results in cell death. Both tyrosinase mRNA amounts and enzymatic dihydroxyphenylalanine (L-DOPA) oxidase activity are consistently reduced at the injection site in GCV-treated animals compared with phosphate buffered solution (PBS)-treated ones ($p<0.01$), indicating destruction of melanocytes at the local injection site.

Nucleoside Analogs

Nucleoside analogs that may be useful for administration according to the subject technology include the following:
 deoxyadenosine analogues: didanosine (ddI), vidarabine
 adenosine analogues: BCX4430
 deoxycytidine analogues: cytarabine, gemcitabine, emtricitabine, lamivudine, zalcitabine
 guanosine and deoxyguanosine analogues: abacavir, acyclovir, entecavir, ganciclovir, valganciclovir (prodrug guanosine analog)
 thymidine and deoxythymidine analogues: stavudine (d4T), telbivudine, zidovudine (azidothymidine, or AZT)
 deoxyuridine analogues: idoxuridine, trifluridine.
 Ganciclovir Ganciclovir (9-[(1,3,-dihydroxy-2-propoxy)methyl] guanine, or DHPG) is a synthetic, acyclic purine analog of the nucleoside guanosine. It is structurally and pharmacologically like acyclovir and is active against herpes viruses. The drug is a prodrug, converted intracellularly to ganciclovir 5'-monophosphate by a viral kinase, e.g., one is encoded by the cytomegalovirus (CMV) gene UL97 during infection.

Subsequently, cellular kinases catalyze the formation of ganciclovir diphosphate and ganciclovir triphosphate, which is present in 10-fold greater concentrations in CMV or herpes simplex virus (HSV)-infected cells than uninfected cells. Compared to acyclovir, ganciclovir differs structurally such that it has substantially increased antiviral activity against cytomegalovirus (CMV) and less selectivity for viral DNA.

Ganciclovir triphosphate is a competitive inhibitor of deoxyguanosine triphosphate incorporation into DNA and preferentially inhibits viral DNA polymerases more than cellular DNA polymerases. In addition, ganciclovir triphosphate serves as a poor substrate for chain elongation, thereby disrupting viral DNA synthesis by a second route.

The active phosphorylated form of ganciclovir inhibits replication of CMV and other human herpesviruses by interfering with DNA synthesis through competition with deoxyguanosine for incorporation into viral DNA and by terminating DNA synthesis at the point of incorporation. Ganciclovir inhibits viral DNA polymerases more effectively than it does cellular polymerase. Chain elongation resumes when ganciclovir is removed. In CMV-infected cells, ganciclovir is thought to be phosphorylated much more rapidly than in uninfected cells; however, uninfected cells can also produce low levels of ganciclovir triphosphate. Concentrations of ganciclovir triphosphate may be as much as 100-fold greater in CMV-infected than in uninfected cells and may persist for days in the CMV-infected cell.

Valganciclovir is an oral prodrug that is rapidly converted to ganciclovir and plays a major role in the treatment and prevention of CMV infections in immunocompromised hosts.

Gene Therapy Vectors

Viral Vectors

Viruses such as Adenovirus (AV), adeno-associated virus (AAV), retrovirus, and lentivirus have been found to efficiently transport genes into the cornea. Adenovirus and retrovirus can successfully deliver genes into the cornea, for example, for short periods of time with mild-to-severe inflammatory responses. However, both of these vectors are of limited use for gene therapy because of their inability to transduce low/non-dividing cells such as corneal endothelium and keratocytes, and induction of immune reactions. AAV and disabled lentivirus vectors offer better alternatives for delivering genes into eye tissues because of their ability to transduce slow/non-dividing cells and ability to provide long-term transgene expression. The origin of lentivirus vectors (equine infectious anemia virus and HIV) is a concern and significantly dampens enthusiasm for its use in human patients. Among viral vectors, AAV is a good choice for gene therapy because of their potency and safety profile. Recombinant AAV vectors have shown great promise for ocular gene therapy and restoring vision in patients with no major side effects.

Adeno-Associated Virus

Among 110 identified AAV serotypes, serotypes 1-10 have been used to date for gene therapy. AAV vectors have demonstrated high transduction efficiency and long-term transgene expression in the retina, cornea, and many non-ocular tissues in vivo. AAV2 has been tested more in-depth compared to other AAV serotypes for gene therapy, although each serotype has shown unique transduction patterns for various cells/tissues. AAV6, -8 and -9, especially, have the ability to mediate whole-body gene transfer efficiently. The variation in gene transfer by different AAV serotypes is likely due to interactions between host-cell receptor and viral capsid. Structural variations in the capsid region of different AAV serotypes enable each serotype to bind different cell surface receptors. For instance, AAV serotypes 4, 5, and 6 use sialic acid, whereas AAV 8 and 9 use laminin receptors to enter cells. This led to the development of hybrid AAV vectors as a variety of pseudopackaged vectors were produced using transencapsidation of the AAV2 genome into the capsid of AAV1-9. These next generation hybrid vectors AAV2/1-9, displayed greater transduction efficiency compared to AAV2/2 in ocular tissues of various animal models.

After vector introduction into the eye via intravitreal and subretinal injection, AAV2/7 and 2/8 demonstrate superior long-term transduction ability (up to 6 months) in both retinal and anterior chamber tissues including the iris, trabecular meshwork, and cornea. Subsequent studies with AAV2/6, AAV2/7, AAV2/8, and AAV2/9 vectors further reinforced these finding for retinal tissue. In a similar fashion, AAV2/8 and 2/9 demonstrate 5-100-fold superior transduction efficiency in non-ocular tissues such as heart, brain, skeletal muscle, lung, and liver.

AAV2/6, AAV2/8, and AAV2/9 vectors encoding alkaline phosphatase (AP) efficiently transduce human corneal fibroblasts, but differ in transduction efficiency. AAV2/6 displays 30-50-fold higher transduction efficiency compared to AAV2/8 or AAV2/9. None of the tested AAV serotypes induce significant cell death or loss of cellular viability, reaffirming that AAV vectors are safe for the cornea. Studies with these vectors using mouse cornea in vivo and human cornea ex vivo show very different transduction profiles compared to in vitro investigations. Contrary to in vitro findings, the order of transduction efficiency for the three tested vectors was found to be AAV2/9≥AAV2/8>AAV2/6. These findings are not surprising, as literature reports imply that in vitro gene delivery may differ from in vivo transduction. None of the three tested serotypes cause any significant side effects such as cell death, loss of cellular viability, inflammation and/or noticeable immune reaction in the cornea as measured with TUNEL and CD11b or F4/80 immunostaining. Transgene expression in the corneal epithelium was detected up to 8 months with AAV2 in the mouse eye, suggesting that rAAV-delivered transgenes can persist for several months, and possibly years, in vivo.

The AAV-DJ (type 2/type 8/type 9 chimera), engineered from shuffling eight different wild-native viruses, has been used for gene transduction due to highly efficient gene transfer into a broad range of cell types. For example, the AAV-DJ vector has been used to knock out a gene in porcine fibroblasts with a higher targeting frequency than the other naturally occurring serotypes. AAV-DJ outperforms all other serotypes at transduction efficiency in human keratinocytes.

And of the aforementioned or other appropriate AAV vectors can be used according to principles of the subject invention, depending on factors such as dosage and duration of exposure to tissues.

Nonviral Vectors

Introduction of plasmid DNA expressing therapeutic genes into target cells without use of viruses falls under the broad category of nonviral gene transfer methods. Nonviral gene therapy is considered safer than viral gene therapy due to low toxicity, immunogenicity, and pathogenicity. Additionally, plasmid vector production is straightforward and cost-effective. Nevertheless, low transfection efficiency is a major issue. A brief description of these techniques follows.

Microinjection

Using the cornea as an example, plasmid via microinjection has led to successful delivery of genes including GFP, interleukin (IL)18, Flt23k, endostatin, MMP14, and vasohibin into various cells of the cornea. Microinjections targeting different layers of the cornea have been performed at various anatomic locations and include intrastromal, subconjunctival, and directly into the anterior chamber. Microsurgical techniques also offer a feasible method of exploring gene function in corneal disorders. Successful transgene delivery in the cornea in vivo has occurred using intrastromal lamellar implantation of a partially dried p-bFGF—SAINT-18 complex composed of SAINT-18 and plasmid vector encoding reporter or FGF2 gene. This corneal gene transfer method permitted localized transgene delivery in the cornea.

These same techniques for plasmid or naked DNA insertion may be applied to the iris, through microinjection or otherwise, according to principles of the subject technology.

Electroporation

Electroporation, also known as electrogenetherapy or electropermeabilization, makes use of high-intensity electrical pulses to form transient pores in the cell membrane and is useful for gene delivery in both cultured eye cells and ocular surface tissues in vivo. An advantage is large DNA constructs can be transported into cells although specialized equipment is necessary. Again using the cornea as an example, electroporation has the ability to deliver foreign genes into the corneal epithelium as well as keratocytes. Electrical current of 200 V/cm did not cause trauma, corneal edema, or inflammation but introduced transgene at low levels. Higher electrical current resulted in enhanced gene transfer but also led to considerable corneal damage. Electrical current can cause irreversible tissue damage as a result of thermal heating or Ca2+ influx due to disruption of cell membranes. Electrically assisted gene delivery to the endothelium of ex vivo human corneas has been described. Using custom-designed electrodes, two reporter genes, EGFP and beta-galactosidase (βgal), were successfully transported into human corneas in organ culture using eight 1-Hz 100-ms pulses of 125 mA square current. Although efficiency was much lower than viral vector, low cell death and no remarkable change in tight junction integrity of endothelial cells show its potential clinical application. The electrotransfer of glyceraldehyde-3-phosphate dehydrogenase (GAPDH) small interfering RNA (siRNA) and dextran macromolecules into mice corneal epithelium in vivo using iontophoresis and electroporation individually and in combination has been reported. Although both iontophoresis and electroporation independently delivered macromolecules into the cornea, iontophoresis was found to be more efficient and the combination of iontophoresis followed by electroporation was more effective than both methods alone.

Sonoporation

Sonoporation employs ultrasound waves to create pores in the plasma membrane in order to deliver DNA to the nucleus. Ultrasound is effective for cell transfection in vitro and in vivo. Transfection efficiency of this approach is dependent on the transducer frequency, acoustic pressure, output strength, and pulse duration of ultrasound treatment in addition to the use of contrast agents such as microbubbles. Microbubbles were generated as contrast agents to not only enhance imaging but also improve gene delivery efficiency by boosting cell permeability. Ultrasound-targeted microbubble destruction may hold great potential as a site-specific gene transfer approach and has been used successfully in AAV-mediated gene transfection of human RPE cells in vitro and rat retina in vivo.

Gene Gun

Gene gun is a ballistic (also called bioballistic) gene transfer method. It utilizes micron-sized biologically inert heavy metal (gold, silver or tungsten) particles and mechanical or macroprojectile (centripetal, magnetic or electrostatic) force. The bombarding of DNA-coated particles on cells/tissues with high velocity results in gene transfer. Gene delivery with gene gun depends on many factors such as amount of DNA-coated on particles, temperature, number of cells, amount of force, number of DNA-coated particles, etc. Shallow penetration of particles, substantial cell damage, uncontrolled gene transfer, high cost, access to internal organs, etc. are few among many limitations of this method.

Microinjection, electroporation, iontophoresis, sonoporation, and gene gun techniques for plasmid or naked DNA insertion may be applied to the iris, according to principles of the subject technology and as will be understood and tailored to the circumstance by those of skill in the art.

AAV Vectors for Melanocytes

Adeno-associated virus (AAV) is a helper-dependent parvovirus that is not associated with any known pathology. Recombinant AAV (rAAV) expresses no viral proteins, is able to transduce both dividing and non-dividing cells, and is associated with persistent transgene expression. It has been extensively evaluated as a gene therapy vector with hundreds of patients having received rAAV in clinical trials without any significant vector-associated complications. Unlike gamma-retroviral and lentiviral vectors, integration of rAAV is uncommon, with the vector genome persisting in an episomal state. There are at least twelve serotypes and many capsid variants of rAAV, with different receptor and co-receptor usage resulting in differing tropisms for different cell types.

Although AAV2/2, 2/1, and 2/4 have been successfully used to revert the phenotype of different retinal disease models affecting primarily the retinal pigment epithelium, no transduction of primary human melanocytes was seen with a serotype 2 rAAV vector (rAAV2) in one study. Transduction of murine choroid and iris melanocytes by rAAV serotype 1 following intraocular injection has been reported, suggesting at least some rAAV serotypes might be capable of transducing human melanocytes.

A screen of variants of rAAV for their ability to transduce primary human melanocytes identified rAAV6 as an optimal serotype, transducing 7-78% of cells. No increase in transduction was seen with rAAV6 tyrosine capsid mutants. The number of cells expressing the transgene peaked at 6-12 days post-infection, and transduced cells were still detectable at day 28. Therefore, rAAV6 may be considered a non-integrating vector for transduction of primary human melanocytes.

Besides rAAV1 and rAAV6, any suitable adeno-associated viral vector may be used according to principles of the subject technology.

Gene Vector Carrier

As used herein, "gene vector" or "genetic vector" may refer to one or more polynucleotides or a carrier of that one or more polynucleotide, such as a virus (e.g., the capsid of an adeno-associated virus) carrying nucleic acid sequences of interest (e.g., DNA and/or RNA, genes, promoters, and enhancers), or to the entire combination of that carrier comprising the polynucleotide, and any other proteins or other molecules also being carried.

As used herein, a "gene" has the standard definition and may also refer to a polynucleotide (e.g., DNA or RNA) with a sequence that has sufficient information to encode a particular protein.

As used herein, the term, "thymidine kinase gene" refers to a polynucleotide including a known, standard DNA sequence encoding thymidine kinase in an organism, or a modification thereof. The modification of a known, standard DNA sequence encoding thymidine kinase includes (1) a variation or fragment of the known DNA coding sequence encoding thymidine kinase (e.g., codon-optimized sequence); or (2) a complementary DNA or RNA sequence (including messenger RNA, or mRNA) to the standard DNA coding sequence, that includes sufficient information to result in transcription and/or translation of thymidine kinase or a protein with identical function to thymidine kinase.

As used herein, "operably linked" means that elements for expression are positioned in a vector relative to a coding sequence in such a way as to direct or regulate expression of the coding sequence.

A gene vector (e.g., DNA sequence, plasmid, or viral vector such as AAV) according to the subject technology may be brought by a surgeon to the iris surface by any of various carriers (the "gene vector carrier'), including a fluid solution or suspension, plasma, gel or paste (e.g., applied to the iris surface with a spatula, pledget, or other applicator), or medicated disc, strip, or pledget of biocompatible material, e.g., to which the gene vector is applied to one side, like a medicated bandage. For example, the surgeon can apply one or more discs, strips, or pledgets of such material to the iris surface for a period of time (e.g., 1, 3, 5, 10, 12, or 15 minutes or longer), with the side of the material contacting the iris containing the vector particles that are adherent to it, e.g., by capillary forces or by a biodegradable adhesive, such as a fibrin or albumin paste or glue or other suitable material that quickly dissolves.

Hydrogels and Other Materials to Deliver Gene Vectors

Hydrogels are polymers that have the ability to swell in water or aqueous solvent systems and hold the solvents (intended drugs) in a swollen cross-linked gel phase for delivery. Through manipulation of permeation and diffusion characteristics, they are able to retain hydrophobic and hydrophilic agents, small molecules, and macromolecules. Depending on the specific structure, they can be nondegradable or degradable in application. Hydrogels have the ability to retain hydrophobic, hydrophilic, small molecules, and macromolecules. They can be designed to be temperature and pH-sensitive.

Hydrogels are formed by the crosslinking or self-assembly of hydrophilic polymers, which can be formed from naturally occurring (e.g., fibrin, chitosan and hyaluronan) or synthetic (e.g., polyethylene glycol (PEG) and polyvinyl alcohol) materials. Furthermore, hydrogels can be customized for many applications. For example, they can be designed to be injectable or environmentally responsive, to encourage infiltration of specific cell types and to acquire various geometries. Control over delivery of genetic vectors can be achieved by altering physical properties of the hydrogel carrier, such as pore size and degradation kinetics. Importantly, transgene expression can be designed to enhance or synergize with the intrinsic bioactivity of the scaffold and thereby create an environment that promotes tissue formation for regenerative medicine.

Hydrogels are an especially appealing class of delivery materials for clinical applications of genetic cargos as they can be introduced into the body with minimally invasive procedures. Fibrin PEG and self-assembling peptide hydrogels have been shown to successfully encapsulate and release both AAV and LV. Alginate, a negatively charged biomaterial, is an attractive and versatile vehicle that has also been tested for the delivery of viral vectors due to its low immunogenicity, tunable biodegradability, and gentle gelation procedure. In contrast with other hydrogels used for viral delivery, alginate is particularly appealing for applications where transduction is intended to be obtained outside the polymer network in situ directly within the cellular microenvironment of the tissue target without tissue interaction. Alginate hydrogels are well known for not supporting cell infiltration and adhesion without chemical modifications.

Typically, the release of payloads from alginate hydrogels can be tuned by controlling three key aspects of an alginate hydrogel system: the diffusivity of the payload within the hydrogel; the degradability of the hydrogel; and the affinity between the alginate and the payload. The three aspects above have been used to control the release of small molecules, proteins, and, more recently, larger particles such as viral vectors. AAV and LV display distinct intrinsic physical characteristics, including divergent sizes and surface features. Given these differences it is expected that the mechanism of release from alginate hydrogels vectors will differ between the two vectors. For example, mesh size is a key characteristic of alginate hydrogels that influences diffusivity. Indeed, the reported alginate hydrogel pore sizes range from ~5-170 nm and therefore for cargos that display similar sizes, disruption of the existing polymer network (i.e. degradation) is necessary to modulate the cargo release. Alginate hydrogels can be engineered to degrade on a scale that ranges from days to months by varying the alginate molecular weight composition, mismatch in the size of cross-linking junctions and degree of polymer chain oxidation. Therefore, degradable alginate hydrogels are desirable delivery materials that can be tailored to meet desired release rate of viral vectors such as LV and AAV.

For highly water-soluble payloads, dissolution from a hydrophilic polymeric matrix is primarily controlled by the diffusion of the vector through the hydrogel layer; a high vector concentration gradient within the gel layer facilitates vector delivery. For drug candidates with lower aqueous solubility, however, vector release rate is mainly dependent upon the erosion of the polymeric matrix. As the result, the swelling characteristics of the hydrophilic polymer may significantly influence vector release profiles. In addition, hydration and erosion of the polymer matrix lead to further water intake and penetration; this will subsequently impact vector diffusion.

Iris Delivery Discs Loaded with Hydrogel and Vector Particles

One type of vector carrier device according to the subject technology for carrying the gene vector, e.g., AAV or lentiviral particles, is a flexible strip or "disc" [1] (FIGS. 1A though 1D) carrying a hydrogel or another delivery material [2] (e.g., fibrin or albumin matrix or "glue") in which the vector particles are embedded, encapsulated, or otherwise contained in well, chambers, pockets, columns, or similarly functioning structures. The medium or matrix for releasing the particles can consist of a variety of materials and combinations thereof. The following discussion will focus on hydrogels by way of example, without limiting the materials that may be used for the same vector-releasing purpose according to principles of the subject technology.

Figure 1B:
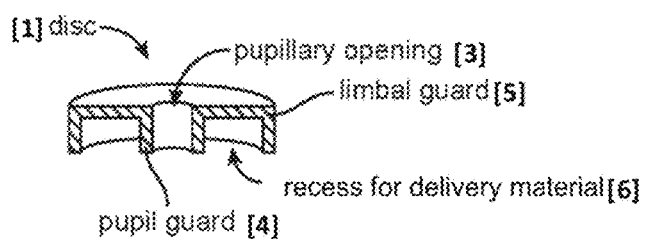
Figure 1C:
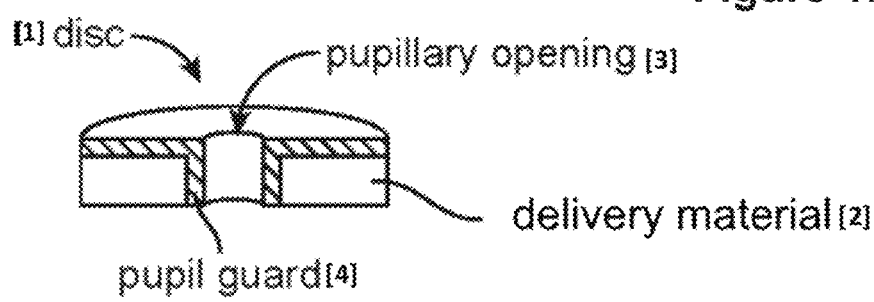
Figure 1D:
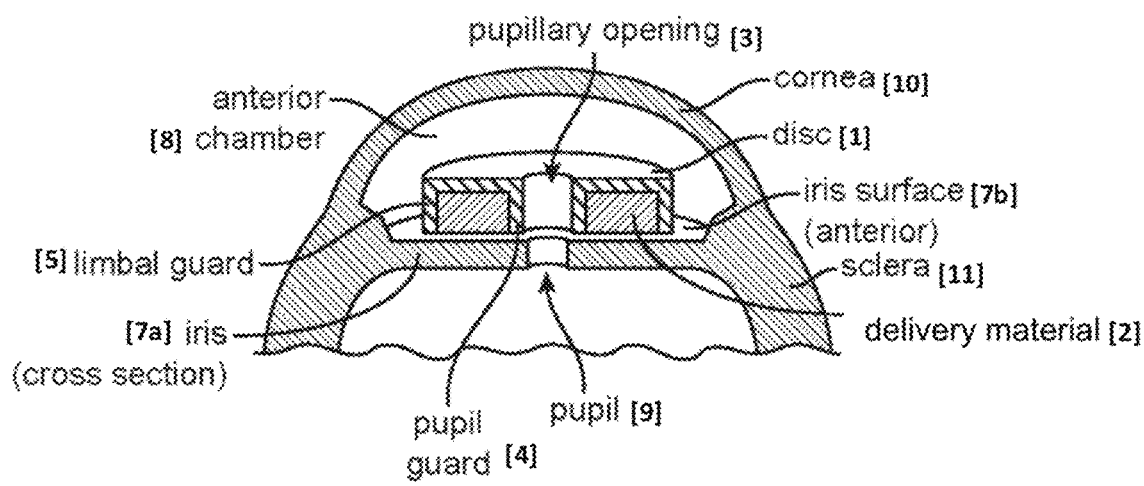

The hydrogel for delivery of the genetic vector is preferably situated on the posterior aspect of the disc [1], facing and contacting the anterior surface of the iris [7b] when the disc [1] is positioned during the procedure (FIG. 1D). The recess [6] for the hydrogel (e.g., delivery material) on the disc is shown in FIG. 1D. The hydrogel begins dissolving after contact with water, e.g., the aqueous humor in the patient's anterior chamber, or after reaching body temperature (37° C.) or pH (7.4). After an initial period of from 0 seconds to 2 minutes or longer, the hydrogel begins releasing the vector particles. The rate of dissolution and release of the particles can be engineered based on a choice of the hydrogel's components and their concentrations and chemistry.

In some embodiments, the hydrogel would begin dissolving or degrading upon contact with aqueous humor in a patient's eye, and after an initial period, e.g., 30, 45, 60, 75, or 90 seconds or longer, to give the surgeon time to place the disc on the patient's iris (e.g., by unfolding the disc and positioning it), the hydrogel would begin releasing the gene vector from the hydrogel. The hydrogel in some embodiments would preferably release the vector quickly, e.g., within 1-3 minutes or less after the initial period has elapsed. This allows the vector to contact the iris soon and in a high concentration or titer, to help ensure successful transduction of iris stromal melanocytes rapidly, making the procedure relatively short in duration.

In some embodiments, the disc is round in shape, sized and shaped to fit the patient's iris. Alternative shapes could also be used, such as polygonal strips. The disc can come in various sizes to fit a variety of iris sizes, or can be standardized to one or a few sizes, e.g., based on statistical averages of iris sizes. A central, pupillary opening in the disc allows aqueous humor to flow through it while the disc rests on the iris and releases the vector during surgery.

Non-limiting examples of the disc described herein are shown in FIGS. 1A-1D. In some embodiments, the disc [1] has a "pupil guard" [4], which is a central, cylindrical protuberance disposed circumferentially around the pupillary opening [3] of the disc [1] (FIGS. 1B though 1D). FIG. 1D shows a schematic of the disc that fits in the iris[7a-7b] of the patient's eye. A central, pupillary opening [3] in the disc [1] allows aqueous humor to flow through it while the disc [1] rests on the iris [7a] and releases the vector during surgery. The pupil guard [4] preferably extends away from the disc [1] toward the iris surface [7b] and creates a barrier between the hydrogel and the pupillary opening [3]. The pupil guard [4] may decrease the risk of vector particles traveling retrograde (relative to aqueous humor flow), from the anterior chamber [8] to the posterior chamber through the pupil [9], during surgery.

In some embodiments, the disc [1] has a "limbal guard," [5] which is a central, cylindrical protuberance disposed circumferentially around the periphery of the disc [1] (FIGS. 1B and 1D). The limbal guard [5] preferably extends away from the disc [1] toward the iris surface [7b] and creates a barrier between the hydrogel and the trabecular meshwork, at the iridocorneal angle of the cornea [10], near the ocular limbus. The pupil guard [4] may decrease the risk of vector particles traveling antegrade (relative to aqueous humor flow), from the anterior chamber into the trabecular meshwork, during surgery.

In some embodiments, the disc has neither a pupil guard nor a limbal guard (FIG. 1A). In other embodiments, the disc has both a pupil guard [4] and a limbal guard [5] (FIGS. 1B and 1D). In some embodiments, the disc has a pupil guard [4] without a limbal guard (FIG. 1C). And in some embodiments, the disc has a limbal guard [5] without a pupil guard (not shown).

Surgery

The following surgical description is only exemplary, not meant to limit the subject technology. Any suitable procedure for administering the gene therapy according to the subject technology may be followed, according to an ophthalmologist's skill, experience, and preferences.

A preoperative miotic such as pilocarpine and/or intracameral miotic agents can be used in patients to maximize the available anterior surface area for contact with the gene vector during the procedure. Moreover, miosis can be beneficial in opening the trabecular meshwork, thereby increasing aqueous humor outflow rate, and increasing the velocity of aqueous flow into the anterior chamber through a smaller pupil vs. a larger one. This higher flow velocity and increased outflow of aqueous humor may lower the risk of exposure of the IPE to free vector particles that may otherwise flow from the anterior chamber through the pupil and to the posterior surface of the iris during and after the procedure.

After suitable local or general anesthesia of the patient is obtained, a corneal paracentesis may be created, and the anterior chamber and angle deepened with viscoelastic or an air bubble. Alternatively, the procedure may be performed by injection of vector particles from a syringe using a needle directly inserted into the anterior chamber with no prior paracentesis. Lidocaine or other local anesthetic may be instilled intracamerally for further anesthesia.

The surgeon introduces the genetic vector carrier into the anterior chamber, either into the full chamber or posterior to a volume of viscoelastic or air bubble. Administering the fluid behind an air bubble, for example, can decrease an amount of injected genetic vector carrier needed to produce a clinical result, increase the likelihood of contact between the DNA vector particles and the anterior iris, and decrease loss of particles into the corneal endothelium or corneal stroma, where the vector, carrying a tyrosinase promoter, would be nonfunctional.

After injection of the genetic vector carrier (e.g., solution, suspension, or medicated strip or disc) of vector particles into the anterior chamber has occurred, the surgeon may wait for an appropriate time period to elapse to ensure adequate surface interaction between the particles and the anterior iris. This time may vary depending on, e.g., the titer (concentration) of particles in the administered fluid, the volume of fluid injected, and the volume of the space within the anterior chamber into which the administered fluid has been placed, e.g., within the entire anterior chamber (the average volume in adults is about 170 μL) or posterior to viscoelastic or an air bubble.

After waiting an appropriate length of time to ensure adequate surface interaction between the vector particles and the anterior iris, the surgeon can withdraw any excess amount or the remainder of the administered genetic vector carrier from the anterior chamber by any appropriate means, such as suction, flushing with an appropriate fluid such as balanced salt solution (BSS), and/or rinsing, etc. This removal of the genetic vector carrier after an appropriate exposure time may be considered a "quenching" of the process, to limit or prevent exposure of remote melanocytes, such as in the IPE, choroid, and RPE, to the genetic vector.

In cases in which an appropriate dose of the vector (e.g., 5-50 uL of a 1E10 to 1E13 vg/ml solution of AAV particles) is injected via needle into the anterior chamber such that no subsequent removal of vector from the anterior chamber is required, any vector that has not been uptaken into iris melanocytes or other cells will leave the anterior chamber by normal egress of aqueous humor, at about 1% per minute, through the trabecular meshwork and uveal scleral outflow systems and into the systemic circulation.

Viscoelastic or the air bubble, if applied, may be removed or irrigated from the anterior chamber, and Carbachol intraocular solution (or other miotic) may be injected intracamerally to produce pupillary miosis. All wounds are hydrated and checked to ensure water-tight closure and a 10-0 nylon suture, for example, is placed in the main wound if necessary. Otherwise the corneal wounds may be self-sealing.

Postoperatively, a nucleoside analog such as ganciclovir or acyclovir (or other appropriate prodrug such as those listed above, chosen based on the suicide gene construct used) should be administered for an appropriate duration, e.g., days to weeks. This drug may be started by the patient preoperatively if the physician chooses. The duration of administration may vary based on patient response, e.g., as her eyes gradually lighten over time, or based on a fixed protocol, e.g., anywhere from 1 to 7 days or 1 to 4 weeks. In some embodiments, a nucleoside analog starts to be administered at least one week, two weeks, three weeks, four weeks, or five weeks after operation. In some embodiments, a nucleoside analog is administered for three days, four days, five days, six days, seven days, eight days, or nine days. In some embodiments, a nucleoside analog is administered on days 5-10, on days 10-15, on days 15-20, on days 20-25, on days 25-30, on days 30-35, on days 35-40 or on days 40-45 after operation. In some embodiments, a nucleoside analog is administered on days 13-17, on days 18-22, on days 23-27, on days 28-32, on days 33-37, on days 38-42, on days 43-47 or on days 48-52 after operation.

The patient should be monitored postoperatively for symptoms and signs of iritis, which may occur as melanocytes die, or other ocular inflammation. Such inflammation is expected to mild and temporary and may be managed with cycloplegics (e.g., cyclopentolate) and topical or systemic corticosteroids (e.g., prednisolone eyedrops or oral prednisone or methylprednisolone dose pack). Pain may be managed with acetaminophen, nonsteroidal anti-inflammatory NSAID drugs like ibuprofen, or, in rare cases, opioids such as oxycodone.

EXPERIMENTAL EXAMPLES

Example 1: In Vivo Study—Selective Removal of Anterior Iris Stromal Melanocytes in Rabbits A Dutch Belted (DB) rabbit was acclimatized and quarantined for 14 days, then received unilateral OD (right eye) 50 µL injection of AAV6 in phosphate buffered solution (PBS) into the anterior chamber at a titer of 2E+13 vg/ml, using a 500 µL insulin syringe with 30 G needle, following general anesthesia with a mixture of ketamine (35 mg/kg) and xylazine (5 mg/kg). Pupils were kept miotic with 2% pilocarpine topical eyedrops during surgery and up to QID for one day postoperatively. On days 38-42, the rabbit received 50 mg/kg ganciclovir injection intraperitoneally. The eyes were examined with slit lamp at days 1, 3, 5, 7, 14, 21, 28, 38, 45, 52, 59, 66, and 83. Flash electroretinography was performed at a baseline and was normal.

In this case, the AAV6 vector carried a self-complementary (double stranded) DNA cassette encoding a Herpes Simplex virus Type 1 (HSV) thymidine kinase (pAL120-TK plasmid sequence, courtesy of Maria Castro, PhD: disclosed in King et al., J Virol. 2008 May 82(9):4680-4; Addgene, Watertown, Mass.), driven by a mouse tyrosinase promoter sequence (pDRIVE5Lucia-mTyr, InvivoGen, San Diego, Calif.). Any other melanocyte-specific gene construct capable of inducing cell death by apoptosis, and/or any other vector (such as a different AAV serotype) delivered according to principles of the subject technology would be suitable, as discussed herein.

No changes during ophthalmic examination were noticed throughout the entire 83-day study and body weights of the subject rabbits were stable during the study. Cornea and iris looked healthy. No inflammatory cell or flare were observed in anterior chamber. Lens was transparent. The conjunctiva, sclera, and posterior segment examination remained normal, with normal appearing vitreous, retina, choroid, and optic nerve, for the entire duration. We were prepared to treat the injected eye with topical 0.1% dexamethasone (Dexamethasone, WZF POLFA SA, Poland) at the first sign of inflammation in the anterior chamber, but this never occurred.

Before cryo embedding, irides and retinas were washed in 1×TBS and placed to 10%, 20% and 30% gradient sucrose solution made in 1×PBS. Later, tissues were frozen by embedding them in O.C.T. (cryo embedding solution), frozen in liquid nitrogen and kept at −20° C. until further processing. Sections of 10 µm thickness were cut using Leica cryotome CM1860.

Sections of irides and retinas were stained with Hematoxylin & Eosin, Fontana Masson stain kit, and anti-CD68 antibody for identification of macrophages.

Results

Fur: There was no sign of depigmentation in the rabbit's black fur during the study, indicating no significant loss of melanocytes in hair follicles.

Figure 2:
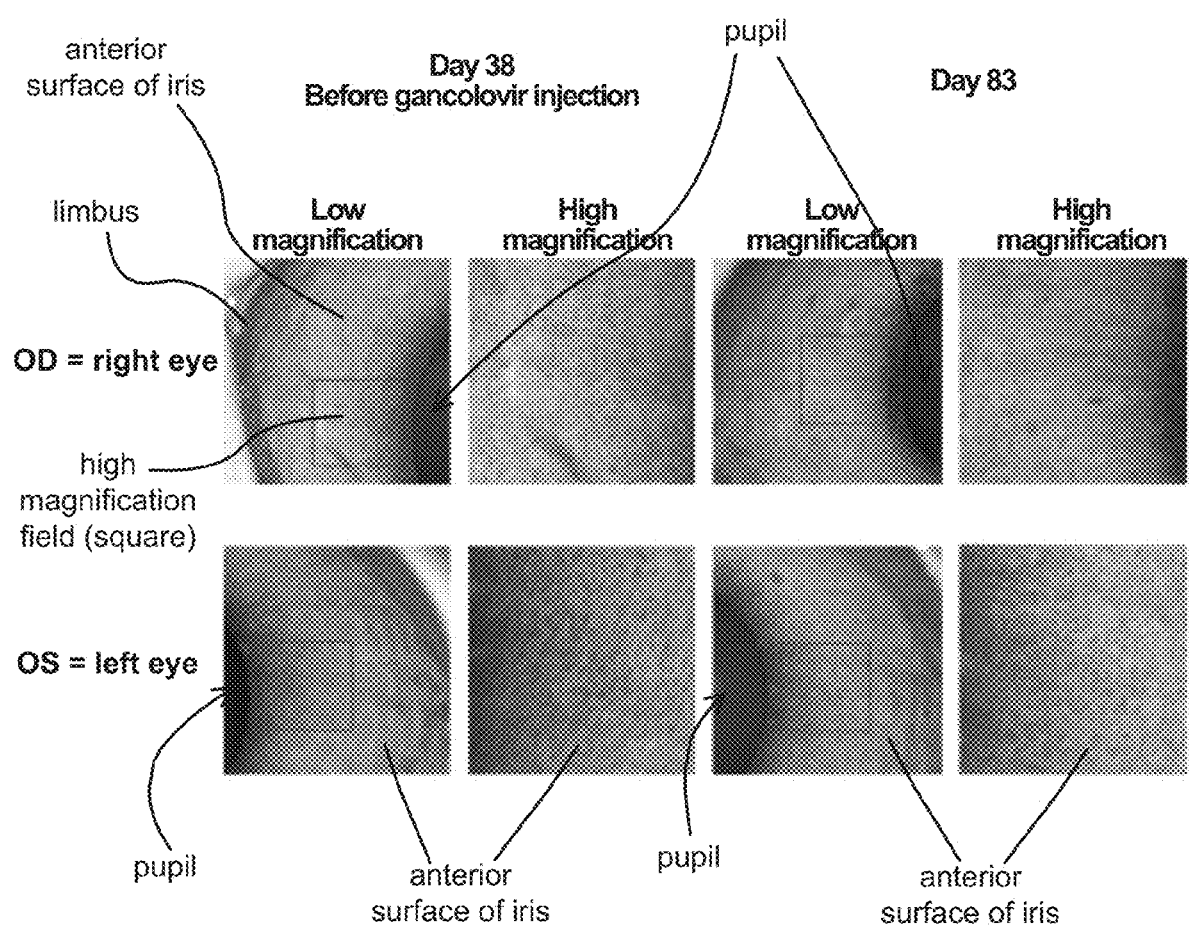
FIG. 2 is a magnified slit lamp view of the iris of both eyes of a rabbit.

Slit lamp examination: On day 45, one week after the Day 38 ganciclovir injection, loss of anterior iris pigmentation was observed, both overall and in a punctate fashion, across the entire surface of the iris in an even distribution. This loss of pigmentation increased at weeks 2 (Day 52) and 3 (Day 59), then stabilized. No further depigmentation was observed by slit lamp examination at 25× magnification between Days 59 and 83. See FIG. 2.

Figure 3:
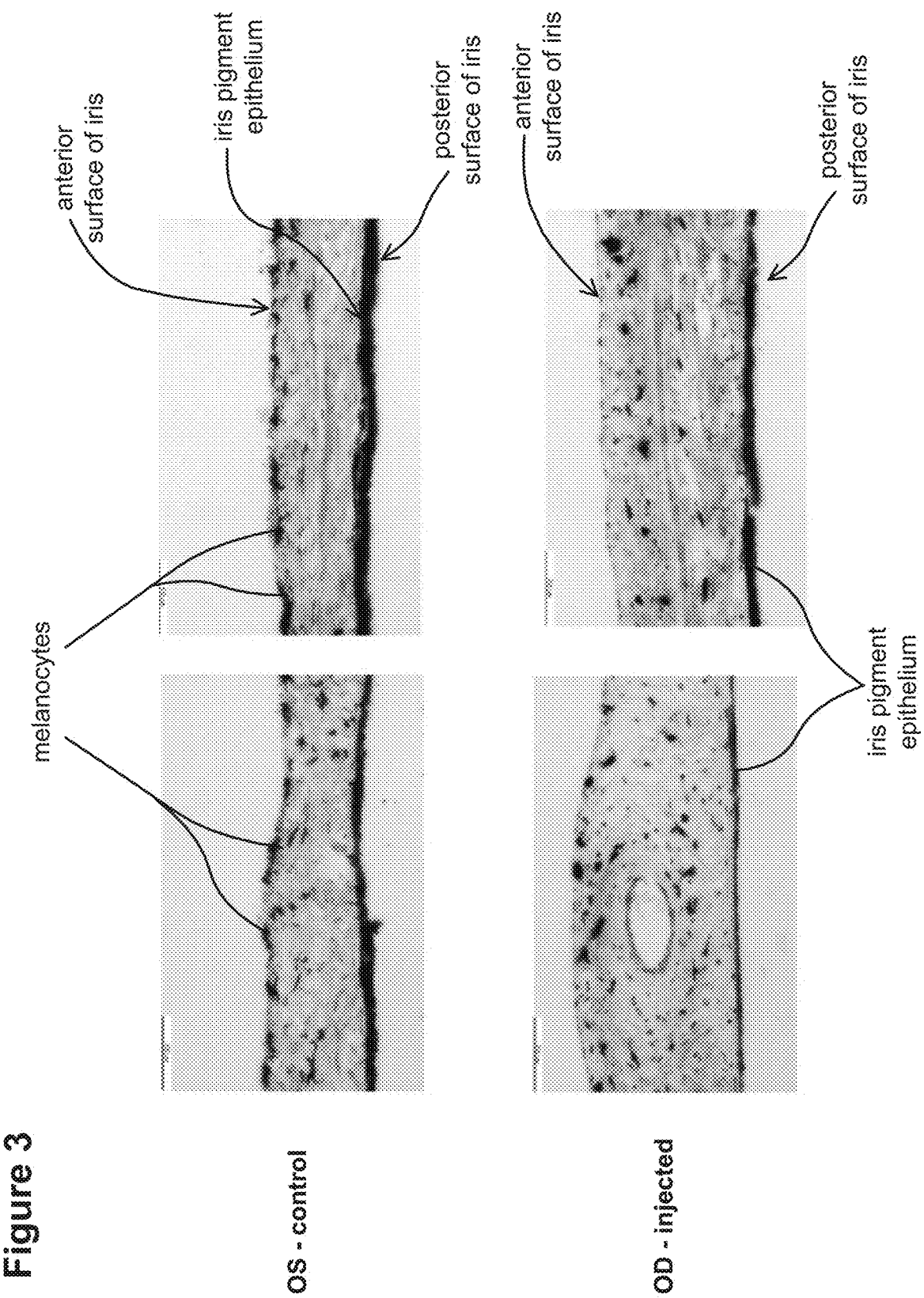
FIG. 3 shows histologic frozen sections of both irises using Fontana-Masson staining.

Histology: Fontana-Masson staining revealed loss of anterior iris stromal melanocytes, especially on the anterior surface of the iris, in the treated eye (OD) relative to the control eye (OS). See FIG. 3. The iris pigment epithelium (at the posterior aspect of the iris) was unchanged, with no observable loss of melanocytes in this region. The retina and choroid also show no loss of melanocytes.

Example 2: In Vivo Study—Eye Color Change in Rabbits

A Dutch Belted (DB) rabbit was acclimatized and quarantined for 14 days, then received unilateral OD (right eye) 50 µL injection of AAV6 in phosphate buffered solution (PBS) into the anterior chamber at a titer of 2E+13 vg/ml, using a 500 µL insulin syringe with 30 G needle, following general anesthesia with a mixture of ketamine (35 mg/kg) and xylazine (5 mg/kg). AAV6 vector containing a coding sequence of a Herpes Simplex virus Type 1 (HSV) thymidine kinase as described above in Example 1 was used.

Pupils were kept miotic with 2% pilocarpine topical eyedrops during surgery and up to QID for one day postoperatively. One rabbit received 50 mg/kg ganciclovir injection intraperitoneally on days 7-11, and the other rabbit received 50 mg/kg ganciclovir injection intraperitoneally on days 14-18.

Figure 4A:
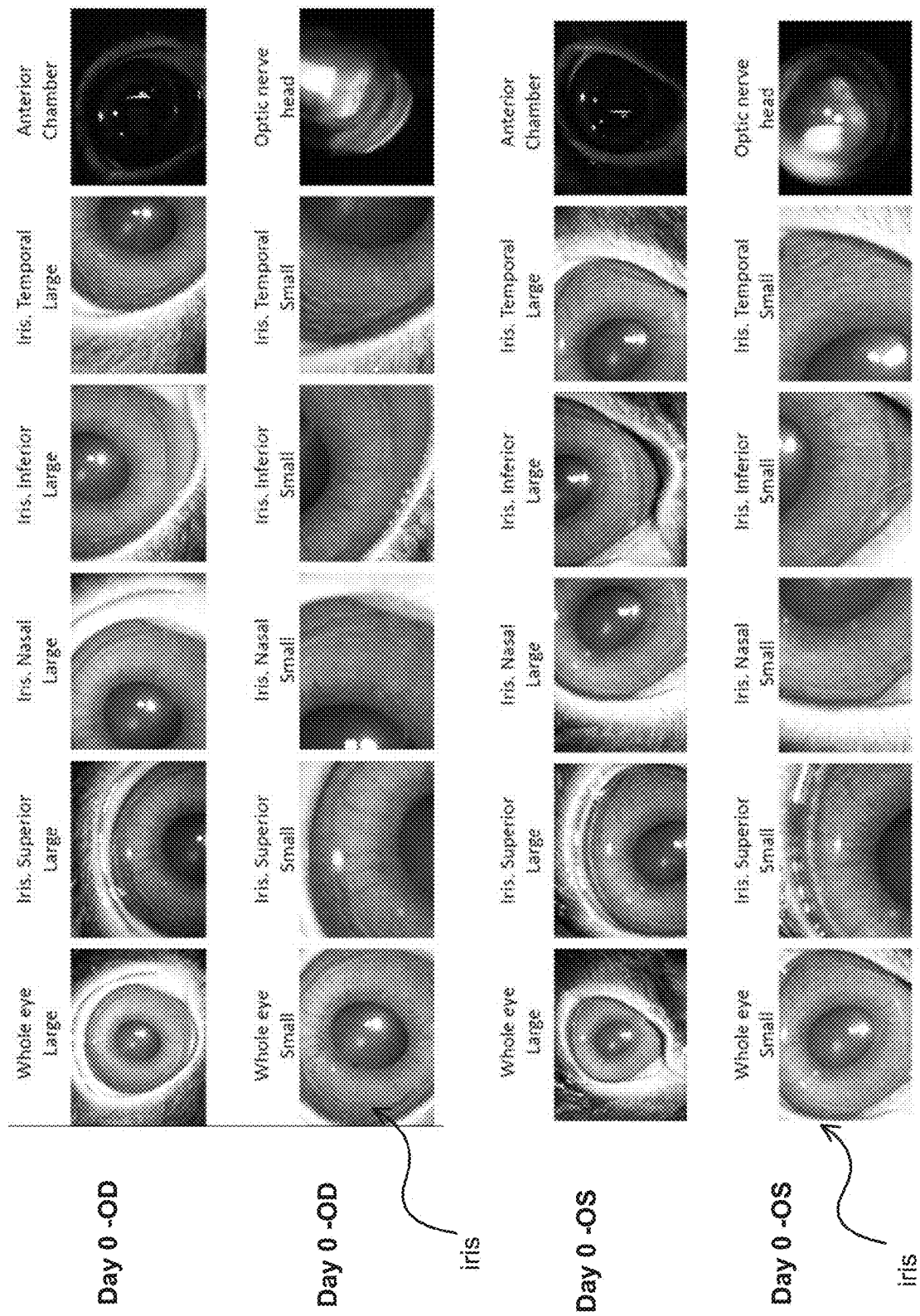
FIG. 4A are pictures of OD (injected eye) and OS (control eye without AAV6 injection) of a rabbit treated as described in Example 2, on the day of injection (day 0).
Figure 4B:
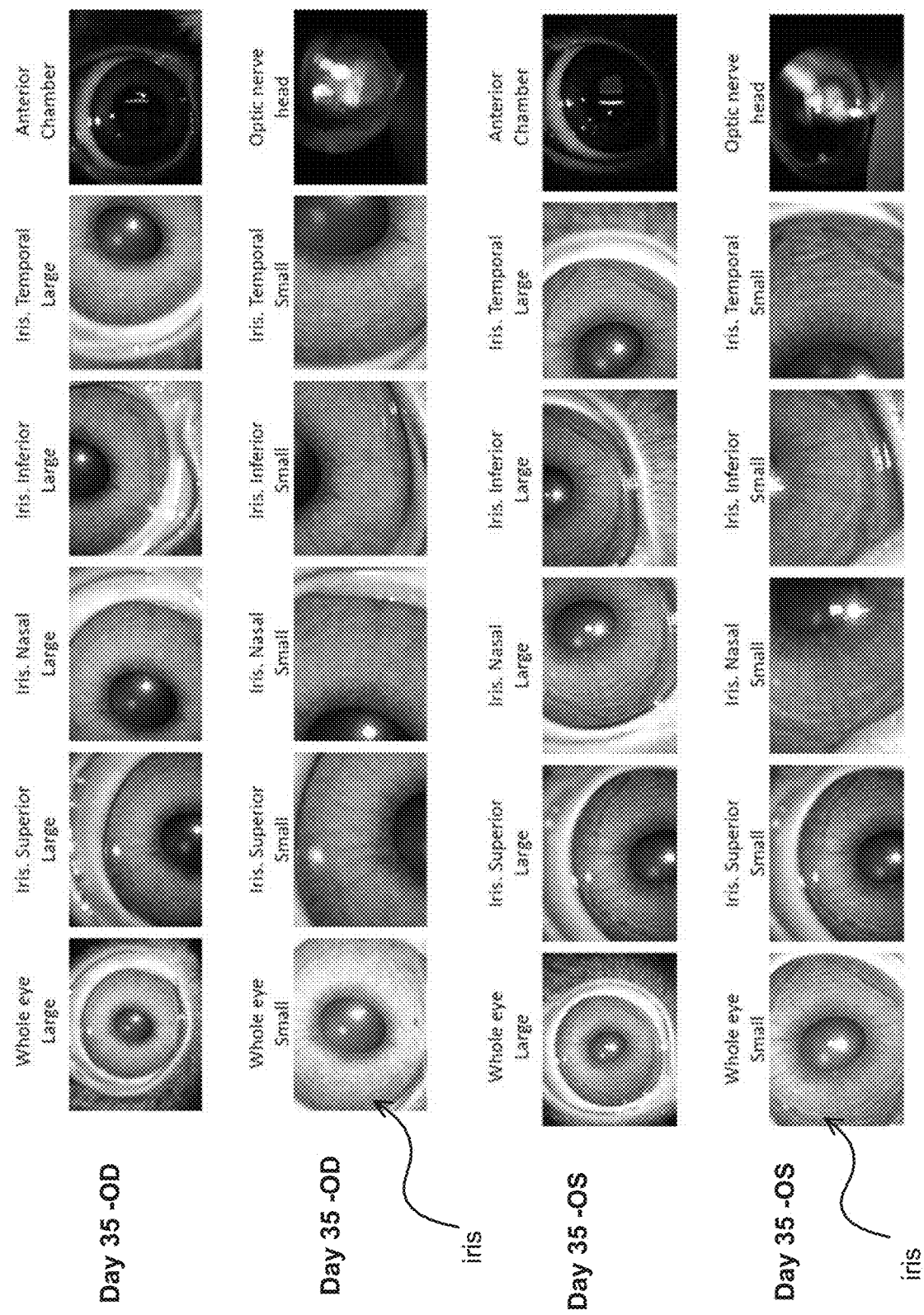
FIG. 4B are pictures of OD (injected eye) and OS (control eye without AAV6 injection) of a rabbit treated as described in Example 2, 35 days after injection (day 35).

The eyes were examined with slit lamp at days 0, 1, 3, 7, 14, 21, 28, and 35, and pictures were taken for both OD (injected eye) and OS (control eye without AAV6 injection) on each day. Images from day 0 and day 35 are provided in FIGS. 4A (day 0) and 4B (day 35). FIG. 4B clearly show eye color change in OD (injected eye) but not in OS (control eye), 35 days after the viral injection.

The foregoing description is provided to enable a person skilled in the art to practice the various configurations described herein. While the subject technology has been particularly described with reference to the various figures and configurations, it should be understood these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, "a period of at least" a particular time (e.g., "a period of at least one day") refers to time period having of a duration of at least as long as that time (e.g., a period lasting one day or more in duration).

Any of the methods or systems of administering a genetic vector carrier having a suicide gene and melanocyte-specific gene promoter as described herein may be used, as will be evident to one skilled in the art, for any of the conditions listed in this description of the subject technology. The amounts and timing of exposure to the genetic vector carrier and of drug administration may be altered or titrated according to patient response.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" can include, but does not require, selection of at least one of each item in the series. Rather, the phrase allows a meaning that includes at least one of any one of the items, and/or at least one of any combination of the items, and/or at least one of each of the items. By way of example, the phrase "at least one of A, B, and C" includes at least one of only A, of only B, of only C, of any combination of A, B, and C; and/or of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined, bolded, and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A composition in a unit dose for changing a color of a subject's iris of an eye, comprising: a sterile ophthalmic preparation comprising a genetic vector comprising (a) a suicide gene; and (b) a melanocyte-specific gene promoter operably linked to the suicide gene, wherein the unit dose is sufficient to kill melanocytes in a stroma of the subject's iris of the eye without inducing visible inflammatory cells or flares in the anterior chamber of the eye.

2. The composition in the unit dose of claim 1, wherein the genetic vector is selected from the group consisting of a plasmid, an adenovirus, an adeno-associated virus, and a lentivirus.

3. The composition in the unit dose of claim 1, wherein the genetic vector comprises a recombinant adeno-associated virus.

4. The composition in the unit dose of claim 1, wherein the sterile ophthalmic preparation is in a powder form, and is reconstitutable with a fluid to form a sterile ophthalmic solution or suspension.

5. The composition in the unit dose of claim 1, further comprising a biocompatible object comprising the sterile ophthalmic preparation and sized to be placed in contact with a person's the subject's iris.

6. The composition in the unit dose of claim 5, wherein the biocompatible object comprises a disc, strip, or pledget.

7. The composition in the unit dose of claim 1, wherein the suicide gene is selected from the group consisting of (i) a herpes simplex virus thymidine kinase (HSVtk) gene; (ii) a cytosine deaminase gene; (iii) a nitroreductase gene; and (iv) a carboxypeptidase G2 gene.

8. The composition in the unit dose of claim 1, wherein the melanocyte-specific gene promoter comprises a tyrosinase (Tyr) promoter.

9. The composition in the unit dose of claim 1, wherein the suicide gene comprises a HSVtk gene, and the melanocyte-specific gene promoter comprises a Tyr promoter.

10. The composition in the unit dose of claim 1, wherein the unit dose comprises 5-50 µL of the sterile ophthalmic preparation comprising 1E10 to 1E13 vector genomes (vg)/ml of the genetic vector.

11. The composition in the unit dose of claim 1, wherein the sterile ophthalmic preparation is suitable for injection directly into the anterior chamber of the eye.

12. A pharmaceutical composition for changing a color of a subject's iris of an eye, comprising:
 a sterile ophthalmic preparation comprising an effective dose of a genetic vector comprising (a) a suicide gene; and (b) a melanocyte-specific gene promoter operably linked to the suicide gene,
 wherein the effective dose is sufficient to: change color of the subject's iris of the eye and kill melanocytes in a stroma of the subject's iris of the eye without inducing visible inflammatory cell or flare in the anterior chamber of the eye, after the pharmaceutical composition is injected directly into the anterior chamber of the eye.

13. The pharmaceutical composition of claim 12, wherein the genetic vector is selected from the group consisting of a plasmid, an adenovirus, an adeno-associated virus, and a lentivirus.

14. The pharmaceutical composition of claim 12, wherein the genetic vector comprises a recombinant adeno-associated virus.

15. The pharmaceutical composition of claim 12, wherein the sterile ophthalmic preparation is in a powder form, and is reconstitutable with a fluid to form a sterile ophthalmic solution or suspension.

16. The pharmaceutical composition of claim 12, wherein the suicide gene is selected from the group consisting of (i) a herpes simplex virus thymidine kinase gene; (ii) a cytosine deaminase gene; (iii) a nitroreductase gene; and (iv) a carboxypeptidase G2 gene.

17. The pharmaceutical composition of claim 12, wherein the melanocyte-specific gene promoter comprises a Tyr promoter.

18. The pharmaceutical composition of claim 12, wherein the suicide gene comprises a HSVtk gene, and the melanocyte-specific gene promoter comprises a Tyr promoter.

19. The pharmaceutical composition of claim 12, wherein the effective dose comprises 5-50 µL of the sterile ophthalmic preparation comprising 1E10 to 1E13 vector genomes (vg)/ml of the genetic vector.

* * * * *

UNITED STATES PATENT AND TRADEMARK OFFICE
CERTIFICATE OF CORRECTION

PATENT NO. : 11,622,927 B2  
APPLICATION NO. : 17/842658  
DATED : April 11, 2023  
INVENTOR(S) : James W. Hill Page 1 of 1

It is certified that error appears in the above-identified patent and that said Letters Patent is hereby corrected as shown below:

In the Claims

In Column 22, in Claim 5, Line 50, after "with" delete "a person's".

Signed and Sealed this  
Fifteenth Day of August, 2023

Katherine Kelly Vidal  
*Director of the United States Patent and Trademark Office*